(12) United States Patent
Felice et al.

(10) Patent No.: US 7,506,797 B2
(45) Date of Patent: Mar. 24, 2009

(54) PUBLIC DROP BOX FOR ISOLATING RECEIVED ITEMS

(75) Inventors: Robert J. Felice, Endicott, NY (US); Michael W. Finney, Endicott, NY (US); Patrick J. Fitzgibbons, Owego, NY (US); Eugene C. Stradley, Owego, NY (US); John T. Swider, Port Crane, NY (US); Louis B. Taylor, Apalachin, NY (US); Michael A. Wisniewski, Owego, NY (US)

(73) Assignee: Lockheed Martin Corporation, Bethesda, MD (US)

( * ) Notice: Subject to any disclaimer, the term of this patent is extended or adjusted under 35 U.S.C. 154(b) by 0 days.

(21) Appl. No.: 11/650,793

(22) Filed: Jan. 8, 2007

(65) Prior Publication Data

US 2007/0108264 A1 May 17, 2007

Related U.S. Application Data

(62) Division of application No. 10/309,541, filed on Dec. 4, 2002, now Pat. No. 7,159,762.

(60) Provisional application No. 60/337,134, filed on Dec. 4, 2001, provisional application No. 60/339,899, filed on Dec. 10, 2001.

(51) Int. Cl.
*B65G 11/04* (2006.01)

(52) U.S. Cl. .............................. 232/45; 232/17; 232/49; 232/52

(58) Field of Classification Search .................. 232/45, 232/47, 49–52, 30–32, 17; 193/8
See application file for complete search history.

(56) References Cited

U.S. PATENT DOCUMENTS 329,688 A 11/1885 Taylor (Continued)

FOREIGN PATENT DOCUMENTS

DE 136666 12/1902

(Continued)

OTHER PUBLICATIONS

U.S. Appl. No. 60/337,134, filed Dec. 4, 2001; Applicants: John T. Swider et al.; Title: Collection Box.

(Continued)

*Primary Examiner*—William L. Miller
(74) *Attorney, Agent, or Firm*—Burns & Levinson LLP; Jacob N. Erlich; Harvey Kaye

(57) ABSTRACT

A publicly accessible drop box for isolating items deposited therein, includes a securable enclosure, a depository port, a closeable container having an opening and located within the securable enclosure, and a closure device for closing the opening prior to removal of the container. The depository port may include a housing forming a reception chamber having an entrance, wherein the housing is rotatably mounted within the drop box. The drop box may include a view port to allow viewing of the opening of the closeable container. The drop box may include a manipulation device extending into the securable enclosure to enable manipulation of the closure device or to enable movement of any items in proximity to the opening of the container.

7 Claims, 10 Drawing Sheets

U.S. PATENT DOCUMENTS

| | | | | |
|---|---|---|---|---|
| 560,477 | A * | 5/1896 | Cook | 232/50 |
| 561,589 | A * | 6/1896 | Hower | 232/49 |
| 570,628 | A * | 11/1896 | Gaschlin | 232/49 |
| 631,105 | A * | 8/1899 | Clouse | 52/339 |
| 634,006 | A * | 10/1899 | Kline | 232/50 |
| 669,624 | A * | 3/1901 | Dickson | 232/50 |
| 777,026 | A * | 12/1904 | Jones et al. | 232/49 |
| 1,299,737 | A * | 4/1919 | Koleta | 232/49 |
| 3,981,436 | A | 9/1976 | Neal | |
| 3,982,690 | A | 9/1976 | Krizan et al. | |
| 4,176,710 | A | 12/1979 | Gansauge et al. | |
| 4,363,438 | A | 12/1982 | Connor | |
| 4,573,416 | A | 3/1986 | Masachika | |
| 4,715,498 | A | 12/1987 | Hanifl | |
| 5,137,212 | A | 8/1992 | Fiterman et al. | |
| 5,316,733 | A | 5/1994 | Rune et al. | |
| 5,400,960 | A | 3/1995 | Jeffs | |
| 5,470,546 | A | 11/1995 | Hall | |
| 5,531,346 | A | 7/1996 | Mosior | |
| 5,979,751 | A | 11/1999 | Maddox | |
| 6,299,061 | B1 | 10/2001 | Henson | |
| 6,742,703 | B2 | 6/2004 | Esakov et al. | |
| 6,918,534 | B2 * | 7/2005 | Fitzgibbons et al. | 232/50 |
| 7,040,529 | B2 * | 5/2006 | Swider et al. | 232/45 |
| 7,114,645 | B2 * | 10/2006 | Felice et al. | 232/31 |
| 7,287,686 | B2 * | 10/2007 | Felice et al. | 232/31 |
| 2003/0106929 | A1 | 6/2003 | Day et al. | |
| 2003/0222132 | A1 | 12/2003 | Esakov et al. | |

FOREIGN PATENT DOCUMENTS

| | | |
|---|---|---|
| DE | 1982064 | 3/1968 |
| DE | 1759533 | 1/1970 |
| DE | 1956059 | 5/1970 |
| GB | 2310422 | 8/1997 |

OTHER PUBLICATIONS

U.S. Appl. No. 60/339,899, filed Dec. 10, 2001; Applicant: Eugene Stradley; Title: Secure Collection Box.

U.S. Appl. No. 60/367,169, filed Mar. 25, 2002; Applicants: John T. Swider et al. Title: Collection Box with Sealable Hamper.

International Search Report, Jul. 23, 2003, PCT/US02/38646.

WO 03/050005, Published PCT International Application, Publication Date Jun. 19, 2003; PCT/US02/39113.

U.S. Postal Service Emergency Preparedness Plan for Protecting Postal Employees and Postal Customers from Exposure to Biohazardous Material etc.; Mar. 6, 2002; publ. by USPS.

* cited by examiner

PUBLIC DROP BOX FOR ISOLATING RECEIVED ITEMS

RELATED APPLICATIONS

The present application is a divisional of U.S. non-provisional application Ser. No. 10/309,541, filed Dec. 4, 2002, now U.S. Pat. No. 7,159,762. The present application claims priority for U.S. Provisional Patent Application Ser. No. 60/337,134, filed Dec. 4, 2001 and entitled COLLECTION BOX, and U.S. Provisional Patent Application Ser. No. 60/339,899, filed Dec. 10, 2001 and entitled SECURE COLLECTION BOX.

FIELD OF THE INVENTION

The present invention generally relates to depository boxes, such as mailboxes, and in particular to such mailboxes which isolate items received therein to prevent the spread of contaminants.

BACKGROUND OF THE INVENTION

The recent incidents of anthrax-laced letters being transported through the United States Postal Service (USPS) facilities by unsuspecting mail handlers to unsuspecting recipients has alarmed the nation and the world. Currently, the tainted letters are discovered after the recipient accepts delivery or by alert postal employees noticing white powder that could be anthrax on mail parcels, sorting and distribution equipment, or themselves. There appear to be no current security devices or procedures that are available to intercept such letters at the earliest source of introduction into the USPS system.

Therefore, it would be advantageous to be able to isolate items dropped into mailboxes and other public drop boxes, so that adequate testing may be performed to detect the presence of any contaminants.

SUMMARY OF THE INVENTION

Accordingly, one embodiment of the present invention provides a publicly accessible drop box adapted for isolating items deposited therein, comprising a securable enclosure, a depository port forming part of the securable enclosure and adapted to allow items to be dropped there through into the securable enclosure, a closeable container having an opening and located within the securable enclosure for receiving items, and a closure device adapted for closing the opening prior to removal of the container from the securable enclosure.

The depository port may include a housing forming a reception chamber adapted for receiving items deposited into the mail box, which housing includes an entrance and is adapted to allow opening of the entrance for receiving deposited items in the reception chamber. The depository port may also include a drop box opening formed as part of the securable enclosure, wherein the housing is rotatably mounted within the drop box for causing exposure of the entrance through the drop box opening by rotational alignment with the drop box opening and for causing closure of the entrance by rotational misalignment with the drop box opening.

The drop box may include a view port located in the securable enclosure and adapted to allow viewing of the opening of the closeable container within the securable enclosure. This view port may be a transparent panel located in a side of the drop box, and be covered by a securable door.

The drop box may include a manipulation device extending into the securable enclosure and adapted to enable manipulation of the closure device or to enable movement of any items in proximity to the opening of the container, by a user located outside the securable enclosure without exposing the user to any said items located within the securable enclosure. This manipulation device may be a hazardous material mitt or glove extending into the drop box and having an open end for manual insertion, which open end is sealed to a side of the securable enclosure to isolate a user of the mitt or glove from items within the drop box. The open end of the hazardous material mitt or glove may be sealed to a transparent panel in a side of the drop box, which panel forms a view port into the securable enclosure.

The closeable container may be a standard size mail flat tray having a rectangular open top and a top cover adapted for engaging the rectangular open top and preventing air from escaping from the container. The closure device may include a door hinged to the top cover and adapted to be left open for receiving articles, and further adapted for closure prior to removal of the container from the securable enclosure.

The drop box may include a duct forming a channel for directing items from the depository port to the opening of the container, and a shutter mounted to the securable enclosure and adapted for closing the channel. This duct and a side of the securable enclosure may form a chamber adapted for storing the shutter in an open position. The shutter may be adapted for removable coupling to the container to provide closure of the shutter with the removal of the container from the securable enclosure.

The closure device of the drop box may be adapted to close the opening of the container during removal of the container from the securable enclosure. A cover may be included and adapted to engage and close the container during removal of the container from the securable enclosure. The drop box may further include a pair of opposed horizontal rails adapted for engaging the container within the securable enclosure and further adapted to engage the cover during removal of the container from the securable enclosure. The drop box may further include second and third securable doors located in opposing sides of the drop box and oriented generally orthogonally to the horizontal rails, wherein the horizontal rails and the second and third doors are adapted to allow simultaneous insertion of one closeable container into the drop box and removal of another closeable container.

In another embodiment, the present invention provides a depository port structure for a publicly accessible mail box, including a housing forming a reception chamber adapted for receiving items deposited into the mail box, which housing includes an entrance and is adapted to allow opening of the entrance for receiving deposited items in the reception chamber. The depository port may also include a drop box opening formed as part of the securable enclosure, wherein the housing is rotatably mounted within the drop box for causing exposure of the entrance through the mail box opening by rotational alignment with the mail box opening and for causing closure of the entrance by rotational misalignment with the mail box opening.

The housing may include an exit from the chamber, and may further be adapted to open the exit by rotation of the housing after the closure of the entrance. The depository port structure may further include a closure surface affixed to the mailbox in a position to block the exit while the entrance is exposed through the mailbox opening. The housing may be rotatable in a first direction to a first position of alignment between the entrance and the mailbox opening and further rotatable in a second direction to a second position wherein the exit is open. This housing may be balanced to rest in the second position. The reception chamber entrance may be directed generally upwardly from the reception chamber and the exit may be directed generally downwardly from the reception chamber to enable gravitational movement of items through said chamber.

The housing may include a flange extending away from the reception chamber entrance in both directions of rotation of the housing, and this flange may be adapted to isolate a user of the drop box from items that have previously passed through the depository port.

BRIEF DESCRIPTION OF THE DRAWINGS

The present invention is illustratively shown and described in reference to the accompanying drawings, in which.

DETAILED DESCRIPTION OF THE DRAWINGS

Figure 1:
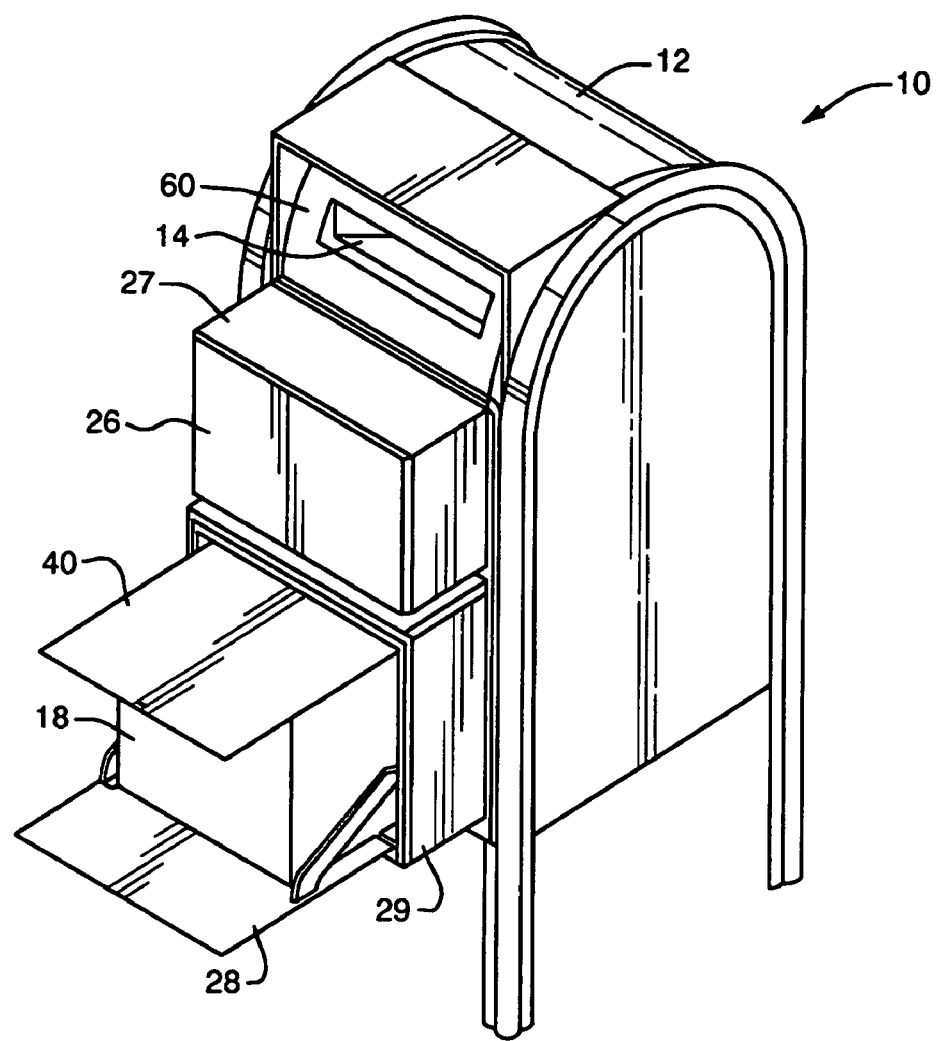
FIG. 1 is a perspective view of a public drop box constructed in accordance with one embodiment of the present invention.
Figure 2:
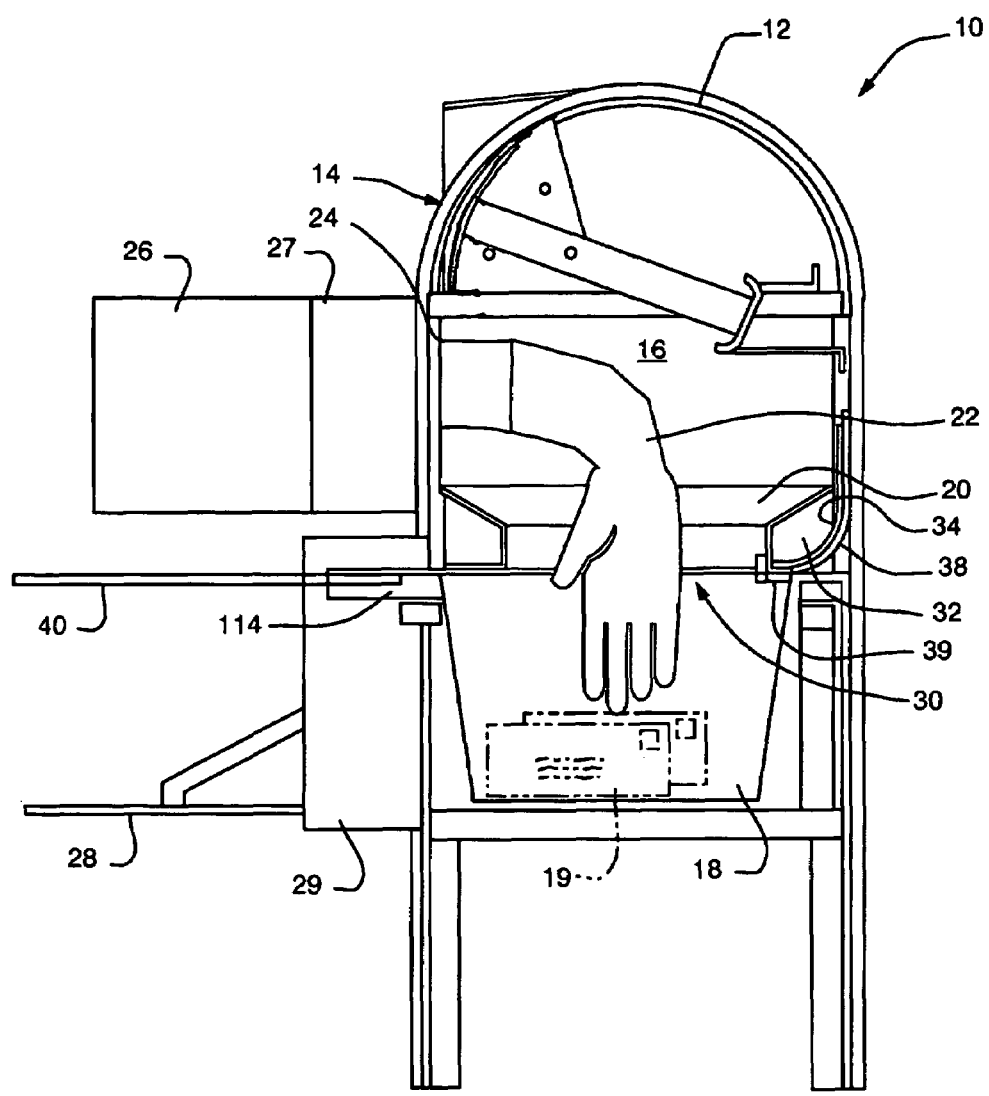
FIG. 2 is a side view diagram of the inside of the public drop box of FIG. 1.

FIGS. 1 and 2 are perspective and diagrammatic views, respectively, of a mail box 10 constructed in accordance with one embodiment of the present invention for isolating items deposited therein. Mail box 10 generally includes a securable enclosure 12 having a depository port 14 and forming a central chamber 16 in which is located a closeable container 18 for receiving deposited mail articles 19. Mailbox 10 also includes a duct 20, which forms a channel for directing deposited mail articles into container 18.

A manipulation device 22 is shown extending into securable enclosure 12, in the form of a hazardous material glove or mitt. Manipulation device 22 is mounted to a side 24 of mailbox 10 and access thereto is controlled by a securable door 26. Securable door 26 is shown hinged to an additional housing 27, which may be used for the storage of manipulation device 22 while mail box 10 is available for public deposits of mail articles. Housing 27 may be retrofitted to a standard mailbox.

Another securable door 28 is used to allow for the removal and replacement of container 18. Securable door 28 opens downwardly to provide support for container 18 upon removal from mail box 10. Door 28 is affixed to an additional housing 29 for the purpose of retrofitting to standard mailboxes.

Duct 20 defines an opening 30 to container 18 for the purpose of directing deposited mail articles into container 18. Duct 20, in combination with mailbox 10, forms a chamber 32 for enclosing a shutter 34 used for closure of the opening 30. The movement of shutter 34 within chamber 32 is directed by an arcuate guide 38. Shutter 34 may also be removeably attached to container 18 by a coupling 39 to cause opening and closure by the insertion and removal of container 18, respectively. Shutter 34 may also be opened and closed by a linkage connected to door 28. Manipulation device 22 may be used to open and close shutter 34. Manipulation device 22 also allows mail articles, that are piled up in container 18, to be cleared from opening 30 so that container 18 may be closed prior to or during its removal from mail box 10.

A separate cover 40 is also shown for engaging container 18 as it is removed from mailbox 10. Cover 40 is removed while container 18 is located within mailbox 10 and engages container 18 as container 18 is removed from mailbox 10.

In operation, mailbox 10 becomes a publicly accessible drop box adapted for isolating items deposited therein. Mailbox 10 forms a securable enclosure 12 having depository port 14 adapted to allow items to be dropped through depository port 14 into securable enclosure 12. Closeable container 18 is located within mailbox 10 for receiving deposited mail articles 19. Container 18 has a closeable opening in the form of shutter 34 or cover 40, and a closure device is provided for closing this opening prior to or during removal of container 18 from mail box 10.

Mail box 10 may further include duct 20 forming a channel for directing items from depository port 14 to the opening of container 18, which opening 30 may thereby be defined by duct 20. Shutter 34 therefore provides one form of closure device for closing the opening 30. Duct 20 and the side of mailbox 10 may form a chamber for storing shutter 34 in an open position.

Mail box 10 may further include manipulation device 22 extending into the enclosure 12 and being adapted to enable manipulation of the closure device by a user located outside of mail box 10 or to enable movement of any deposited items in proximity to the opening 30 of container 18 and thereby facilitate closure of the opening.

Figure 3:
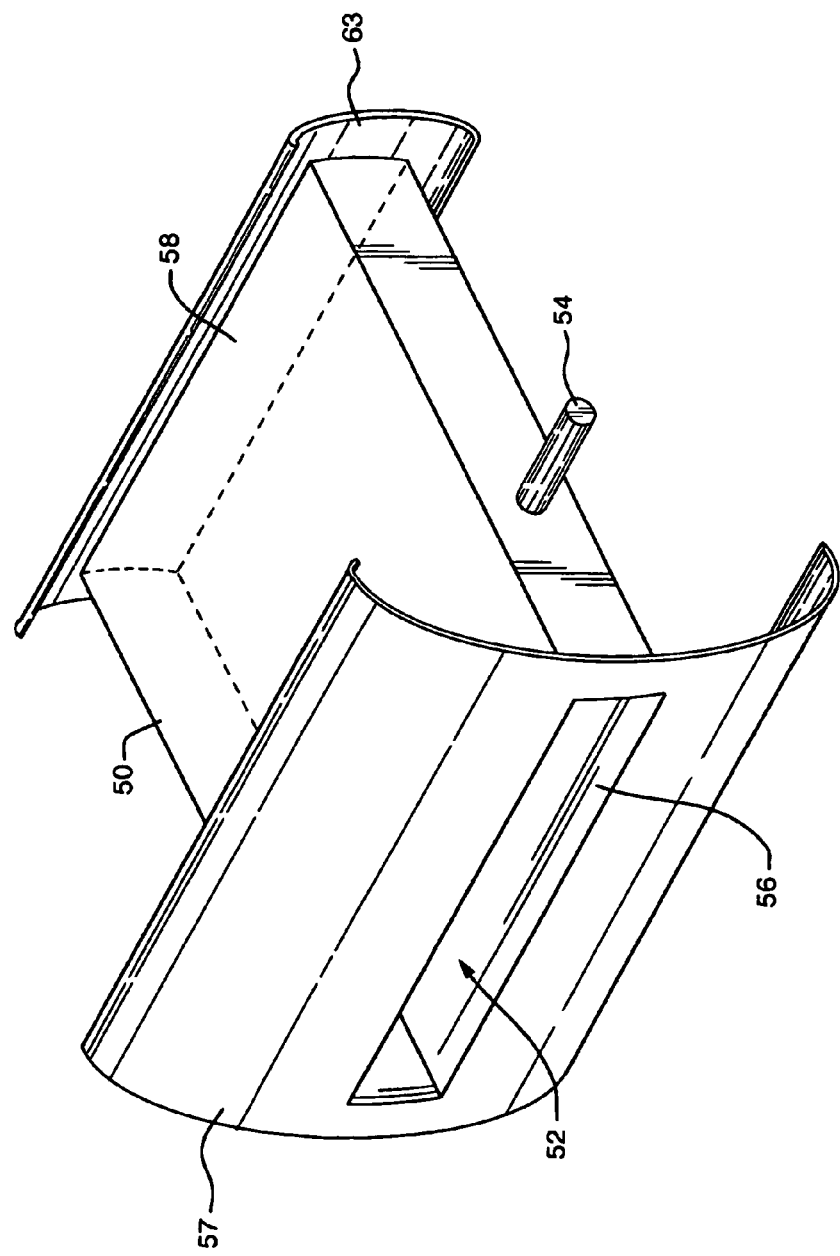
FIG. 3 is a perspective view of a portion of the drop box of FIGS. 1 and 2.
Figure 4:
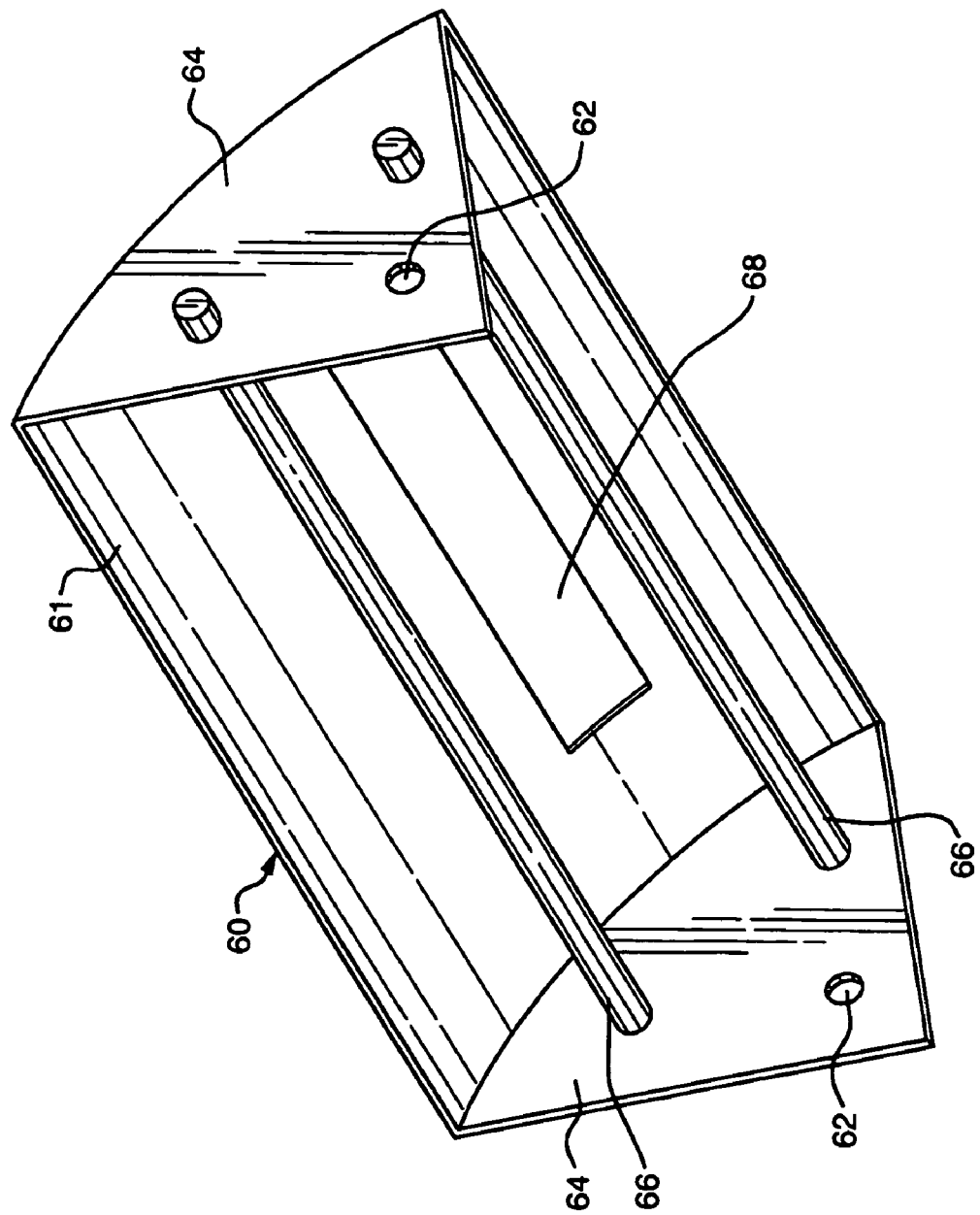
FIG. 4 is a perspective view of another portion of the drop box of FIGS. 1 and 2.

Depository port 14 is shown in greater detail in FIGS. 3 and 4. Depository port 14 primarily includes a housing 50 forming a chamber 52, which is adapted for rotation about an axis or axel 54. Chamber 52 generally includes an entrance 56 and an exit 58 (shown in phantom). Housing 50 also includes a partial shield or flange 57 extending in opposite directions of rotation for housing 50 from each side of entrance 56 as well as a flange 63.

FIG. 4 shows a shield 60 which may be retrofitted to a common mail box by suitably affixing shield 60 over the typical opening used at the top of mail boxes, as shown in FIG. 1. Shield 60 provides a means for rotatably mounting housing 50 at openings 62. Shield 60 generally includes an arcuate member 61, which is affixed to and bounded by a pair of end plates 64. End plates 64 are generally normal to the axis of rotation of housing 50. Shield 60 further includes a pair of stabilizing rods 66 mounted between end plates 64. Rods 66 further provide rotational limitation to housing 50. Arcuate portion 61 includes an opening 68 which forms a depository opening in mail box 10 when shield 60 is affixed in the position shown in FIGS. 1 and 2.

Figure 9:
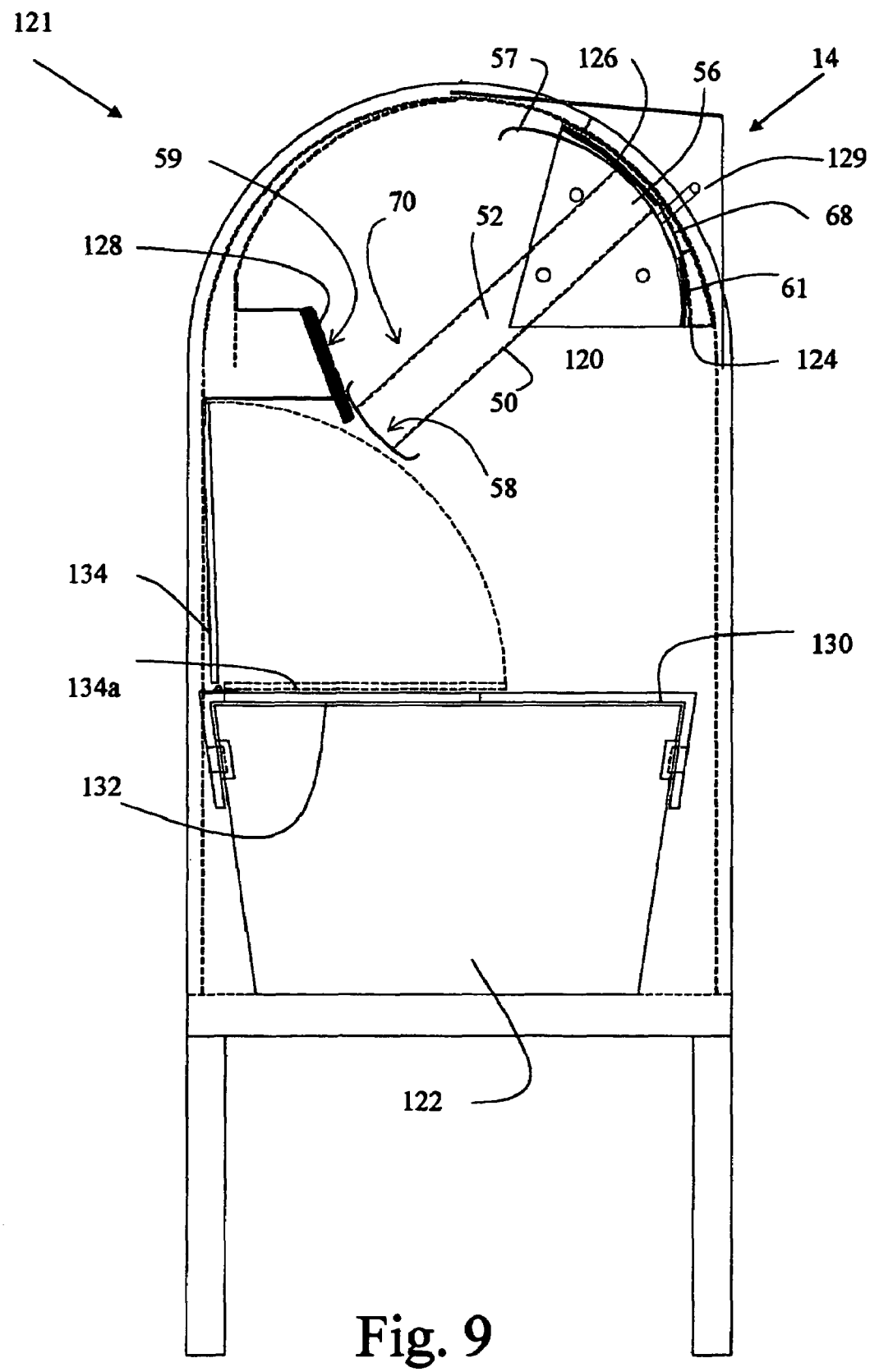
FIG. 9 is a side view diagram of the interior of a drop box constructed in accordance with another embodiment of the present invention.
Figure 10:
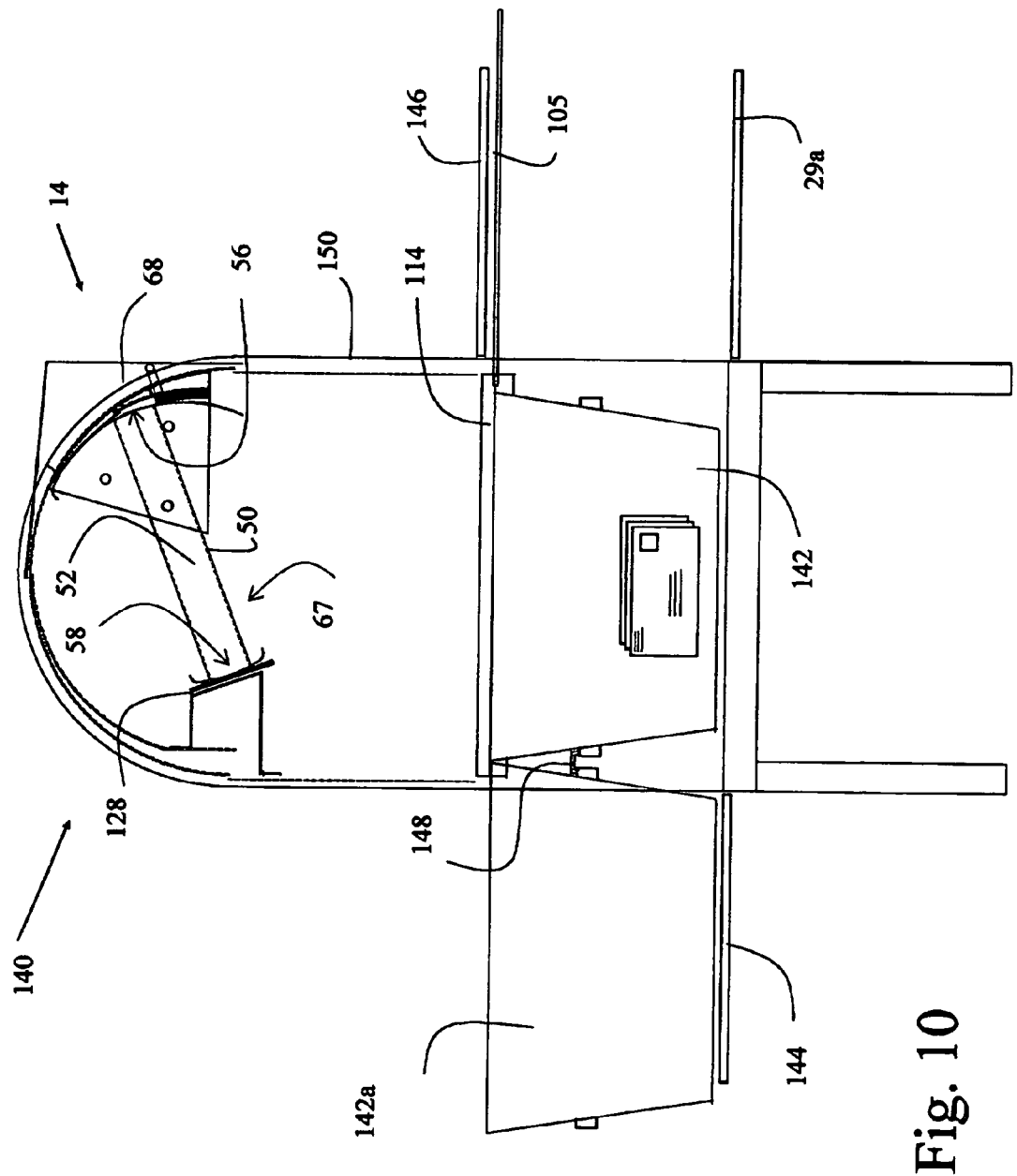
FIG. 10 is a side view diagram of the interior of a drop box constructed in accordance with yet another embodiment of the present invention.

When housing 50 and shield 60 are properly installed as shown in FIGS. 9 and 10, housing 50 is rotatable in one direction (clockwise) to a first position 67 (FIG. 10), to cause exposure of entrance 56 by alignment with mail box opening 68. Housing 50 is further rotatable in a second (counterclockwise) direction to a second position 70 (FIG. 9), for causing the misalignment of entrance 56 with opening 68 and thereby the closure of entrance 56. Housing 50 is balanced to rest in position 70 (FIG. 9) when not in use, which further insures that any mail within chamber 52 passes through exit 58.

Mail box 10 further includes a closure surface 59 (FIG. 9) which is affixed to mail box 10 and located to cause closure of exit 58 when housing 50 is in the first rotational position 67 (FIG. 10) and entrance 56 is open. As shown in FIGS. 9 and 10, entrance 56 of reception chamber 52 is directed generally upwardly from chamber 52 and exit 58 is directed generally downwardly from chamber 52 to enable gravitational movement of items through chamber 52.

In this manner, housing 50 forms another embodiment of the present invention, namely a depository port structure for a publicly accessible mailbox. Housing 50 forms a reception chamber 52 adapted for receiving items deposited into mail box 10, which housing 52 includes an entrance 56 to chamber 52 and is adapted to allow opening of entrance 56 for receiving deposited items in reception chamber 52. Depository port 14 may also include a drop box opening 68 formed as part of securable enclosure 12, wherein housing 50 is rotatably mounted within drop box 10 for causing exposure of entrance 56 through drop box opening 68 by rotational alignment with drop box opening 68 and for causing closure of entrance 56 by rotational misalignment with drop box opening 68.

Housing 50 further includes an exit 58 from chamber 52 and is adapted to open exit 58 by rotation of housing 50 after closure of entrance 56. Closure surface 59 is affixed to mailbox 10 in a position to block exit 58 while entrance 56 is exposed through the mailbox opening 68. Also in this manner, housing 50 is rotatable between a first position of alignment between entrance 56 and opening 68 and a second position 70 wherein exit 58 is open. Housing 50 is further balanced to assume a rest position 70. Flange 57, which extends away from entrance 56 in both directions of rotation of housing 50, is adapted to isolate a user of drop box 10 from items previously passed through depository port 14.

Figure 5:
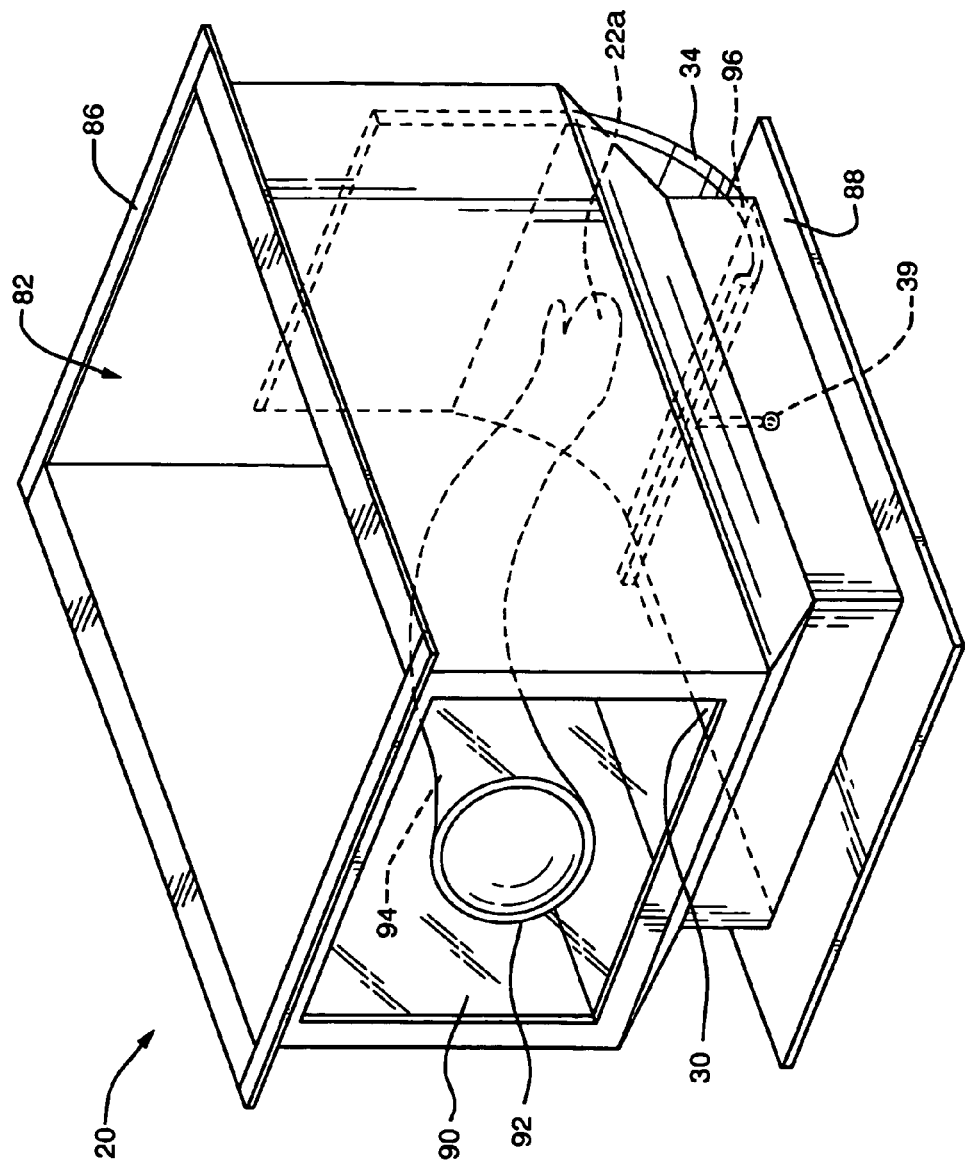
FIG. 5 is a perspective view of yet another portion of the drop box of FIGS. 1 and 2.

Duct 20 is shown in FIG. 5 in a form that may be retrofitted to a standard mailbox. Duct 20 is rectangular in shape and includes an upper opening 82 and a lower opening 30 as identified in FIG. 1. As mentioned, opening 30 defines a closeable opening for a mail container 18. It is desirable to restrict the opening of opening 30 to a size which is smaller than the dimensions of a container 18 so that deposited mail will all be directed into container 18 and not fall in between container 18 and the sides of mail box 10 (FIG. 2). Duct 20 further includes an upper flange 86 and a lower flange 88 which are affixed to mail box 10 to further define the securable enclosure of mail box 10. FIG. 5 also shows shutter 34 passing through an opening 96 in the side of duct 20 to partially close opening 30. Coupling 39 is used to connect shutter 34 to container 18 (FIG. 2).

One side of duct 20 is formed by a clear or transparent panel 90 that thereby creates a view port into the securable enclosure 12 and specifically provides visual access to opening 30. Transparent panel 90 may be made from a variety of durable plastic materials, such as Lexan®. Transparent panel 90 further includes an opening 92 formed therein for allowing a hazardous material glove or mitt 22a to be affixed thereto. The hazardous material mitt 22a includes an open end 94 which coincidences with and is sealed along opening 92 in transparent panel 90. This enables manual insertion into mitt 22a while isolating a user of mitt 22a from items located within the securable enclosure 12.

In this manner, a view port is provided in the form of transparent panel 90 located in a side of securable enclosure 12 and is adapted to allow viewing of the opening 30 within securable enclosure 12. A securable door 26 (FIGS. 1 and 2) is further provided to cover transparent panel 90. Manipulation device 22 may thus take the form of a hazardous material mitt 22a or glove (FIG. 2) extending into mail box 10 and having open end 94 for manual insertion, which open end 94 is sealed to a side of mail box 10 to isolate a user of mitt 22a or glove from items within mail box 10. Open end 94 may be sealed to transparent panel 90 that forms a view port into securable enclosure 12. Shutter 34 may be included and adapted for closing the opening 30, and duct 20 and a side of securable enclosure 12 may form a chamber adapted for storing shutter 34 in an open position.

Figure 6:
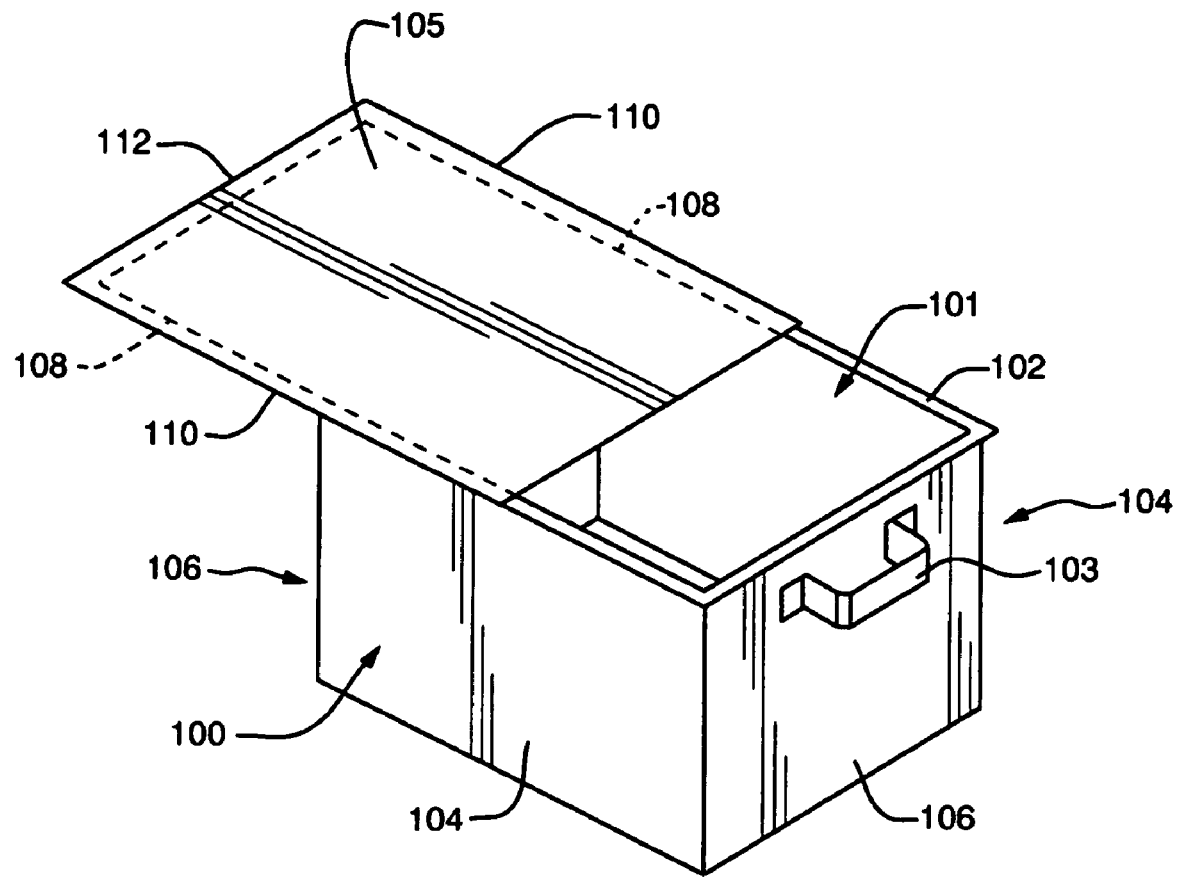
FIG. 6 is a perspective view of a receptacle for receiving deposited items in the drop box of FIGS. 1 and 2.

FIG. 6 is a perspective few of a closeable container 100 identical to container 18 of FIG. 2, being partially closed by a cover 105 (identical to cover 40 of FIG. 2). Container 100 is approximately the size of a standard mail flat tray and has an open top 101. Container 100 includes a handle 103 and a circumferential flange 102 which extends horizontally outward from open top 101 on both opposing sides 104 as well as ends 106 of container 100. Circumferential flange 102 is used for sealing cover 105 to container 100. Cover 105 includes a lip 108 (shown in phantom) along opposing sides 110 and one end 112. Lip 108 is adapted to engage flange 102 of container 100 in the manner shown.

Figure 7:
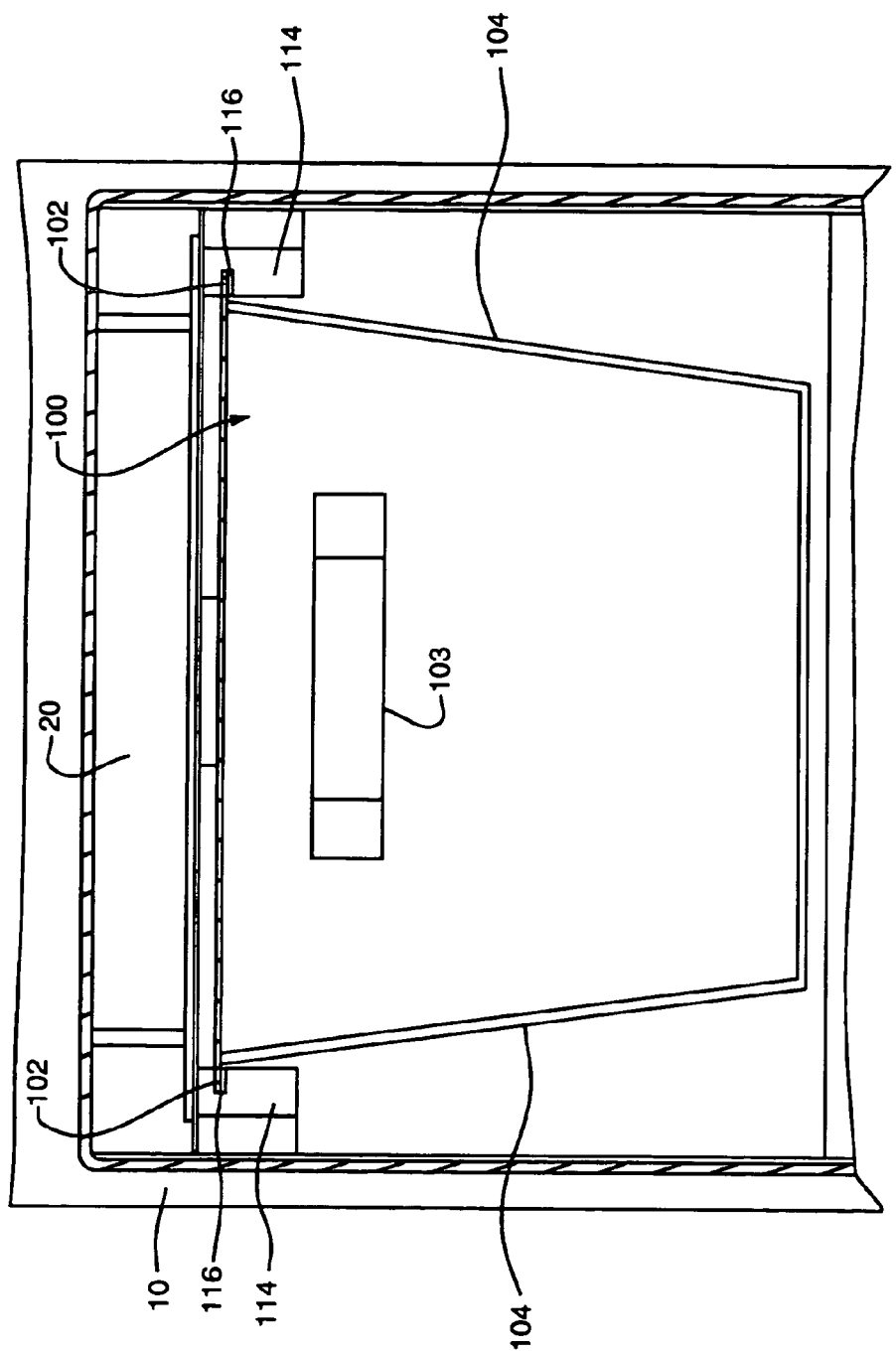
FIG. 7 is a different side view diagram of a portion of the interior of the drop box of FIGS. 1 and 2.
Figure 8:
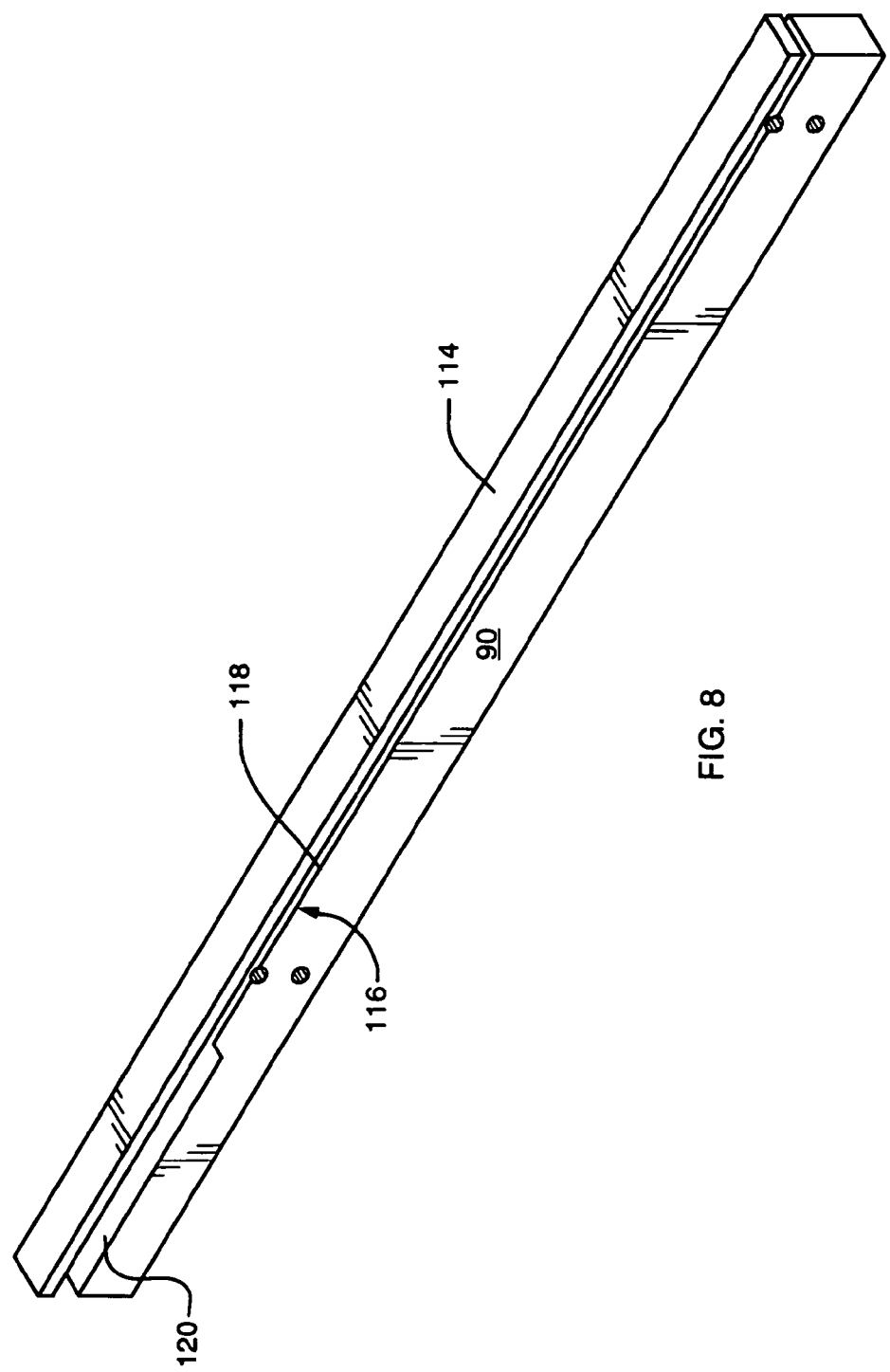
FIG. 8 is a perspective view of an internal element of the drop box of FIGS. 1 and 2.

FIG. 7 shows a side view of a portion of the mail box 10 of FIG. 1, which portion includes the closeable container 100 without a cover. Flange 102 is engaged by a pair of guide rails 114. Guide rails 114 are affixed to mail box 10 to engage the flange 102 on opposing sides 104 of container 100 and to support container 100 in close proximity to duct 20. Guide rails 114 each include a slot 116 for accepting flange 102 (FIG. 6). A guide rail 114 is shown in greater detail in FIG. 8, with slot 116 including a narrower portion 118 and a wider portion 120. Narrow portion 118 is located within the main body of mailbox 10 (FIG. 2), and wider portion 120 is located in extension housing 29 (FIG. 2). In of this manner, wider portion 120 is adapted to handle both flange 102 and cover 105. In practice, cover 105 is located within wider portion 120 and container 18 is pulled from mail box 10 by handle 103 to maintain isolation of the contents of container 100 by closing container 100 with cover 105 as it is withdrawn from mail box 10.

In this manner, container 100 may be a standard size mail flat tray having a rectangular open top 101. A closure device in the form of cover 105 is thereby adapted to engage and close open top 101 during removal of container 100 from securable enclosure 12 and substantially prevent air from escaping from container 100. Also, a pair of opposed, substantially horizontal rails 114 are provided and adapted for engaging container 100 within securable enclosure 12. Guide rails 114 are further adapted to engage cover 105 during removal of container 100 from securable enclosure 12.

FIG. 9 is a side view diagram of another embodiment of the present invention generally including a mailbox 121, a depository port 14 and a closeable container 122. The same reference numbers are used to identify elements that are substantially identical in previous drawings. Depository port 14 is shown with housing 52 located in rest position 70. Depository port 14 is shown in greater detail with a multiplicity of gaskets 124, 126, and 128. Gaskets 124 and 126 are compressible and located between flange 57 and arcuate portion 61 of shield 60. In one embodiment, gaskets 124, 126 and 128 are made from Neoprene® rubber, although any comparable material may be used. In this manner, airborne particulate contamination located within mailbox 121 is prevented from escaping through depository port 14. Depository port 14 is also shown to include a handle 129 for user operation.

Container 122 is shown to be generally rectangular and include a cover 130 for closing the top thereof. Cover 130 includes an opening 132 and a door 134 hinged to cover 130 and adapted to close opening 132. Mailbox 121 may further include a manipulation device (not shown) to allow closure of door 134 prior to removal of container 122 from mailbox 121.

FIG. 10 is another side view diagram of yet another embodiment of the present invention generally including a mailbox 140, a depository port 14 and a closeable container 142. Housing 50 is shown to be located in a position of rotation 67 wherein entrance 56 is in alignment with opening 68 of shield 60, thereby allowing the deposit of items into the chamber 52 of housing 50. In an operative position, gasket 128 is shown to form closure surface 59 which contacts and blocks exit 58 of chamber 52.

In one embodiment, arcuate shield 61 has a radii of 7.875" and flange 57 has a radii of 7" leaving room for the gaskets or seals 124, 126. Axel 54 is 5" from shield 57, which makes flange 57 swing in an elliptical arc. Gaskets 124 and 126 are in a frictional state in the middle of the travel arc and in compression at each end 67, 70 of the travel arc.

Mailbox 140 includes a pair of securable doors 144, 29a that are located on opposing sides of mailbox 140 and oriented generally orthogonally to horizontal rails 114. Hinged door 144 provides an entrance into mailbox 140 for empty mail container 142a, while door 29a (similar to door 29 of FIGS. 1 and 2) provides an exit for removing full mail container 142.

FIG. 10 also shows the additional door 146 that may be hinged to open downwardly and expose a transparent panel 150 similar to panel 90 (FIG. 5). Hinged door 146 may also be used to support cover 105 during the extraction of mail container 142.

In a this manner, horizontal rails 114 and doors 144, 29a are adapted to allow simultaneous insertion of one container 142a into mail box 140 and removal of another container 142. Empty mail container 142a may also be coupled by a coupling 148 to a full container 142, and container 142 may be pulled from mailbox 140 resulting in the pulling of mail container 142a into mailbox 140. At the same time, a cover 105 may be positioned to engage and close container 142 as it is withdrawn from mailbox 140. Alternatively, empty container 142a may be used for pushing full container 142.

The present invention is illustratively described above in reference to the disclosed embodiments. Various modifications and changes may be made to the disclosed embodiments by persons skilled in the art without departing from the scope of the present invention as defined in the appended claims.

What is claimed it is:

1. A depository port structure for a publicly accessible mail box, comprising:

a housing forming a reception chamber adapted for receiving items deposited into said mail box, wherein said housing includes an entrance and is adapted to allow opening of said entrance for receiving deposited items in said reception chamber;

an opening formed as part of said mail box, wherein said housing is rotatably mounted within said mail box for causing exposure of said entrance through said mail box opening by rotational alignment with said mail box opening and for causing closure of said entrance by rotational misalignment with said mail box opening; and an arcuate shield in which said mail box opening is formed and a flange affixed to said housing and extending away from said reception chamber entrance in both directions of rotation of said housing, wherein said arcuate shield and said flange are adapted to isolate a user of said mail box from items that have previously passed through said depository port structure.

2. The depository port structure of claim 1, wherein said housing includes a exit from said chamber, and further wherein said housing is adapted to open said exit by rotation of said housing after said closure of said entrance.

3. The depository port structure of claim 2, further comprising a closure surface affixed to said mail box in a position to block said exit while said entrance is exposed through said mail box opening.

4. The depository port structure of claim 2, wherein said housing is rotatable in a first direction to a first position of alignment between said entrance and said mail box opening and further rotatable in a second direction to a second position wherein said exit is open.

5. The depository port structure of claim 4, wherein said housing is balanced to rest in said second position.

6. The depository port structure of claim 2, wherein said reception chamber entrance is directed generally upwardly from said reception chamber and said exit is directed generally downwardly from said reception chamber to enable gravitational movement of items through said chamber.

7. The depository port structure of claim 1, further comprising one or more compressible gaskets located between said arcuate shield and said flange.

* * * * *